US012678052B2

(12) United States Patent
Parker

(10) Patent No.: US 12,678,052 B2
(45) Date of Patent: Jul. 14, 2026

(54) EVENT RELATED OPTICAL SIGNAL NEUROIMAGING AND ANALYSIS SYSTEM FOR MONITORING ACTIVITY OF A SUBJECT'S BRAIN

(71) Applicant: CoMind Technologies Limited, London (GB)

(72) Inventor: William Parker, London (GB)

(73) Assignee: COMIND TECHNOLOGIES LIMITED, Garsington (GB)

( * ) Notice: Subject to any disclaimer, the term of this patent is extended or adjusted under 35 U.S.C. 154(b) by 278 days.

(21) Appl. No.: 18/033,443

(22) PCT Filed: Oct. 25, 2021

(86) PCT No.: PCT/GB2021/052758
§ 371 (c)(1),
(2) Date: Oct. 24, 2023

(87) PCT Pub. No.: WO2022/084700
PCT Pub. Date: Apr. 28, 2022

(65) Prior Publication Data
US 2024/0225453 A1 Jul. 11, 2024

(30) Foreign Application Priority Data
Oct. 23, 2020 (GB) ...................................... 2016856

(51) Int. Cl.
*A61B 5/00* (2006.01)
(52) U.S. Cl.
CPC .................................. *A61B 5/0082* (2013.01)
(58) Field of Classification Search
CPC .................................................... A61B 5/0082
See application file for complete search history.

(56) References Cited

U.S. PATENT DOCUMENTS 5,772,587 A * 6/1998 Gratton .............. A61B 5/14552
600/323
2007/0208231 A1* 9/2007 Dipl-Ing .............. A61B 5/1107
600/300
(Continued)

FOREIGN PATENT DOCUMENTS

CN          103606744          2/2014
GB            2579618          1/2020
(Continued)

OTHER PUBLICATIONS

Notification of Transmittal of the International Search Report mailed Feb. 9, 2022, for International Application No. PCT/GB2021/052758 filed Oct. 25, 2021.
(Continued)

*Primary Examiner* — Sean A Frith
(74) *Attorney, Agent, or Firm* — McAndrews, Held & Malloy, Ltd.

(57) ABSTRACT

An event related optical signal, EROS, neuroimaging and analysis system for monitoring activity of a subject's brain, the system comprising: a first wavelength-swept light source configured to provide wavelength-swept emission of coherent light; and a plurality of light detectors; wherein the first wavelength-swept light source is arranged to both: (i) deliver the light towards the subject's brain tissue to be scattered to the detectors, and (ii) deliver the light to each of the detectors via one or more reference channels; wherein each of the light detectors comprises: a first input port arranged to receive scattered light from the subject's brain tissue; a second input port coupled to one of the reference channels to receive reference light from the first light source; a light combiner connected to both the first input port and the second input port for combining the scattered light received from the subject's brain tissue with the reference light received from the reference channel to provide a combined (Continued)

light signal comprising a component at a beat frequency for the scattered and reference light; and signal processing circuitry configured to provide neuroimaging and analysis based on the combined light signal.

25 Claims, 3 Drawing Sheets

(56) References Cited

U.S. PATENT DOCUMENTS

| | | | | |
|---|---|---|---|---|
| 2016/0357007 | A1* | 12/2016 | Swanson ............ | G01B 9/02028 |
| 2019/0336001 | A1 | 11/2019 | Zhou et al. | |
| 2019/0336005 | A1* | 11/2019 | Alford ................ | A61B 5/4064 |
| 2019/0336006 | A1* | 11/2019 | Horstmeyer ....... | A61B 5/14552 |
| 2019/0336007 | A1 | 11/2019 | Ruan et al. | |
| 2019/0336057 | A1* | 11/2019 | Alford .............. | A61B 5/14553 |
| 2019/0336060 | A1 | 11/2019 | Shen et al. | |
| 2020/0113439 | A1 | 4/2020 | Mohseni | |
| 2020/0268252 | A1* | 8/2020 | Litvinova ........... | G06N 3/0495 |
| 2020/0333245 | A1* | 10/2020 | Mohseni ............. | A61B 5/0066 |
| 2021/0290168 | A1* | 9/2021 | Do Valle ............. | A61B 5/6803 |

FOREIGN PATENT DOCUMENTS

| | | |
|---|---|---|
| GB | 2101246.3 | 4/2022 |
| GB | 2101252.1 | 4/2022 |
| GB | 2016856.3 | 11/2022 |
| JP | 2014197768 | 10/2014 |
| JP | WO2017188172 | 11/2017 |
| WO | PCT/GB2021/052758 | 4/2022 |

OTHER PUBLICATIONS

Combined Search and Examination Report from GB Intellectual Property Office for GB2016856.3 mailed Dec. 10, 2020.
PCT Notification of Receipt of Record Copy for International Application No. PCT/GB2021/052758 mailed Nov. 11, 2021.
PCT Notification Concerning Submission Obtention or Transmittal of Priority Document for International Application No. PCT/GB2021/05278 mailed Nov. 12, 2021.
Combined Search and Examination Report from GB Intellectual Property Office for GB2101252.1 mailed Feb. 18, 2021.
Combined Search and Examination Report from GB Intellectual Property Office for GB2101246.3 mailed Feb. 18, 2021.
JP Non-Final Office Action for Patent Application No. 2019-049542, mailed Mar. 14, 2023.

* cited by examiner

EVENT RELATED OPTICAL SIGNAL NEUROIMAGING AND ANALYSIS SYSTEM FOR MONITORING ACTIVITY OF A SUBJECT'S BRAIN

TECHNICAL FIELD

The present disclosure relates to the field of event related optical signal ('EROS') systems and methods for neuroimaging and analysis.

BACKGROUND

Existing neuroimaging techniques include diffuse optical imaging and near-infrared spectroscopy. Such techniques are designed for measuring haemodynamic effects, such as those associated with oxygenation state of haemoglobin in the brain and other effects which manifest in optical absorption characteristics of brain tissue. These techniques may therefore enable an indication of properties of cerebral blood flow to be obtained. While cerebral blood flow may be used to provide an indication of activity occurring in the brain, cerebral blood flow is an indirect indicator of underlying neuronal activity.

It may be preferable to be able to reliably monitor brain activity in other ways, for example to provide additional and/or alternative information to that which may be obtained by monitoring haemodynamic effects.

SUMMARY

Aspects of the disclosure are set out in the independent claims and optional features are set out in the dependent claims. Aspects of the disclosure may be provided in conjunction with each other, and features of one aspect may be applied to other aspects.

In an aspect, there is provided an event related optical signal, EROS, neuroimaging and analysis system for monitoring activity of a subject's brain. The system comprising: a first wavelength-swept light source configured to provide wavelength-swept emission of coherent light; and a plurality of light detectors. The first wavelength-swept light source is arranged to both: (i) deliver the light towards the subject's brain tissue to be scattered to the detectors, and (ii) deliver the light to each of the detectors via one or more reference channels. Each of the light detectors comprises: a first input port arranged to receive scattered light from the subject's brain tissue; a second input port coupled to one of the reference channels to receive reference light from the first light source; a light combiner connected to both the first input port and the second input port for combining the scattered light received from the subject's brain tissue with the reference light received from the reference channel to provide a combined light signal comprising a component at a beat frequency for the scattered and reference light; and signal processing circuitry configured to provide neuroimaging and analysis based on the combined light signal.

Embodiments may enable a wealth of data to be obtained for neuroimaging and analysis of the subject's brain. Each of the detectors may be operable to process scattered light which originated from the first light source to identify one or more scattering events associated therewith. This may enable greater spatial resolution for neuroimaging to be achieved, as the different detectors may be located at different regions on the subject's head. This may also enable a higher percentage of scattered light to be detected, as multiple detectors may be used in a variety of different locations on the subject's head to intercept scattered photons travelling in the direction of those detectors. Embodiments may be arranged so that different beat frequencies occur in the combined light signal, where these different beat signals correspond to differences in optical path length for the scattered light (as compared to that for the reference light). Properties associated with these different beat frequencies (e.g. their values, how much or fast they change etc.) may provide an indication of neural events occurring in the brain, and/or an indication of where in the brain (e.g. at what expected penetration depth) these events are occurring.

The system may comprise a reference light splitter arranged to receive the reference light from the first light source to be delivered to each of the detectors. The reference light splitter may be configured to split the reference light from the first light source between: (i) a first reference channel connected to the second input port of a first detector of the plurality of detectors, and (ii) a second reference channel connected to the second input port of a second detector of the plurality of detectors. The first and second input ports of each detector may comprise inputs to an interferometer, e.g. which is arranged to receive the two incoming light signals and to combine these for identifying one or more interference properties in the resulting combined light signal.

The first light source may be configured to emit coherent light at each of a plurality of different wavelengths during one wavelength sweep. For each wavelength of light emitted by the first light source, each detector may be configured to combine said reference light received from the light source with the scattered light from the subject's brain to provide a combined light signal, so that a plurality of different combined light signals are obtained during one wavelength sweep. One wavelength sweep may comprise one iteration of sweeping through the different wavelengths available to the light source. For example, each light source may be configured to emit light at a plurality of different wavelengths according to a sweeping profile. The sweeping profile may indicate which wavelength of light is emitted at which time, and for how long. One wavelength sweep may comprise one completion of the sweeping profile. The sweeping profile may be repeated a plurality of times for obtaining measurements (e.g. obtaining measurements of the subject's brain tissue may comprise a plurality of measurement sweeps).

The signal processing circuitry of each detector may be configured to provide neuroimaging and analysis based on the plurality of obtained combined light signals. The system may be configured to provide neuroimaging and analysis based on an indication of a value of the beat frequencies in the obtained combined light signals and/or an indication of a change in value of the beat frequencies. The system may be configured to provide neuroimaging and analysis based also on timing data for each of the different wavelengths emitted by the first light source. The timing data may comprise an indication of a sweep rate of the light source, or an indication of e.g. a sweeping profile for the wavelength sweeping of light as emitted by the light source.

The system may comprise a second wavelength-swept light source configured to provide wavelength-swept emission of coherent light. The second wavelength-swept light source may be arranged to both: (i) deliver light towards the subject's brain tissue to be scattered to the detectors, and (ii) deliver reference light to each of the detectors via the one or more reference channels. For each of the light detectors, the light combiner may be configured to combine the scattered light received from the subject's brain tissue with at least one of: (i) the reference light received from the first light source via the reference channel, and (ii) the reference light received from the second light source via the reference channel, to provide the combined light signal. For example, the system may comprise a plurality of different wavelength-swept light sources configured to provide wavelength-swept emission of coherent light, e.g. so that light may be emitted from a plurality of different, separate, locations on a subject's head and detected at a plurality of different, separate, locations on the subject's head. This may facilitate greater spatial resolution, as well as enabling a greater spatial coverage for detecting photons of light.

The system may be arranged so that reference light from the first light source travels less far to reach the detectors than reference light from the second light source. The system may be arranged so that the difference in distance for reference light to travel to the detectors from the first and second light source is selected so that beat frequencies generated by scattered light from the first light source and reference light from the first light source have no, or minimal, spectral overlap with beat frequencies generated by scattered light from the second light source and reference light from the second light source. For example, an expected or average optical path distance for light travelling via the subject's brain may be used to select a reference light optical path distance. The optical path distance for reference light from the first light source may be shorter than for reference light from the second light source, so that the expected beat frequencies for light from the first light source may be higher (e.g. due to a greater difference between the two respective time of flights). Based on the expected, or average, optical path distance/time of flight data, an expected beat frequency range may be defined for light from the first light source. As the reference light from the second light source may travel further to the detector than the reference light from the first source (but this reference light will still have a shorter optical path length than the scattered light), the corresponding expected beat frequency range for light from the second light source may be at lower frequencies, e.g. due to the difference in time of flight (and thus difference in wavelengths of light to be combined) being smaller. The system may be arranged so that the two expected (or average) beat frequency ranges have no, or minimal, overlap. This may enable detectors to process signals from both light sources simultaneously without either light source significantly impeding measurements being obtained from light from the other light source. The optical path length for reference light (from either light source) will typically be shorter than that for light travelling via the subject's brain tissue and to the detector as scattered light (although in some examples an inverse scheme could be applied in which the reference path length will be longer than the scattered path length).

The system may be configured to control operation of the first and second light source so that the two light sources do not emit light of the same wavelength at the same time and/or so that the first light source emits light that is incoherent with light from the second light source. The system may be configured to control the light sources to operate sequentially so that the first light source emits light for a first time period while the second light source does not emit light, and then the second light source emits light for a second time period while the first light source does not emit light, for example wherein at least one of the first and second time period encompasses two or more wavelength sweeps.

The system may comprise a carrier channel combiner arranged to receive reference light from each of the first and second light sources. The carrier channel combiner may be configured to combine the reference light from both the first light source and the second light source onto a carrier channel. The system may comprise a carrier channel separator connected to the carrier channel and to reference channels connected to each of the detectors. The carrier channel separator may be configured to separate light from the carrier channel into its constituent parts so that the reference light from the first light source is provided to each of the detectors via the reference channels and the reference light from the second light source is provided to each of the detectors via the reference channels. The first light source may comprise an output light splitter configured to split the coherent light so that some of the light is delivered towards the subject's brain tissue and some of the light is delivered as reference light to each detector via the one or more reference channels.

The first light source may comprise a plurality of signal delivery channels arranged to receive the emitted light and to deliver said light towards the surface of the subject's head. The first light source may comprise an optical switch configured to selectively apply light to each individual signal delivery channel in turn. The system may be configured to control the optical switch to apply the light to a first of the signal delivery channels for a first time block, and to then apply the light to a second of the signal delivery channels for a second time block. The system may be configured to control the optical switch so that at least one of the first time block and the second time block encompasses two or more wavelength sweeps.

The system may be arranged to be affixed to a subject's head. For example, the system may comprise a membrane arranged for attachment to the subject's head, and wherein each of the reference channels is coupled to the membrane, e.g. wherein each of the reference channels is mechanically supported by the membrane. For each detector, the first input port, the second input port and the light combiner may be provided on one integrated circuit.

In an aspect, there is provided an event related optical signal, EROS, method of performing neuroimaging and analysis for monitoring activity of a subject's brain. The method comprises: using a first light source to provide wavelength-swept emission of light and to deliver said wavelength-swept light towards the subject's brain tissue; and using a plurality of detectors to detect light scattered back from the subject's brain tissue at a plurality of different locations. The first light source is operated to also deliver some of the wavelength-swept light it provides to each of the plurality of detectors as reference light via one or more reference channels. Each of the detectors is operated to combine the reference light received from the first light source via the reference channel with the scattered light received from the subject's brain tissue to provide a combined light signal comprising a component at a beat frequency for the scattered and reference light. The method comprises providing neuroimaging and analysis based on the combined light signal.

The method may further comprise using a second wavelength-swept light source to deliver wavelength-swept light both: (i) towards the subject's brain tissue, and (ii) to each of the detectors as reference light via one or more of the reference channels. Each of the detectors may be operated to combine the scattered light received from the subject's brain with at least one of: (i) the reference light received from the first light source via the one or more reference channels, and (ii) the reference light received from the second light source via the one or more reference channels, to provide the combined light signal. Using the first light source to direct light towards the subject's brain tissue may comprise sequentially providing the light to each of a plurality of different signal delivery channels which direct the light towards different regions of the subject's head.

Aspects of the present disclosure may provide computer program products comprising computer program instructions to program a controller to perform any of the methods disclosed herein.

FIGURES

Some examples of the present disclosure will now be described, by way of example only, with reference to the figures, in which.

In the drawings like reference numerals are used to indicate like elements.

SPECIFIC DESCRIPTION

Figures 1A, 1B:
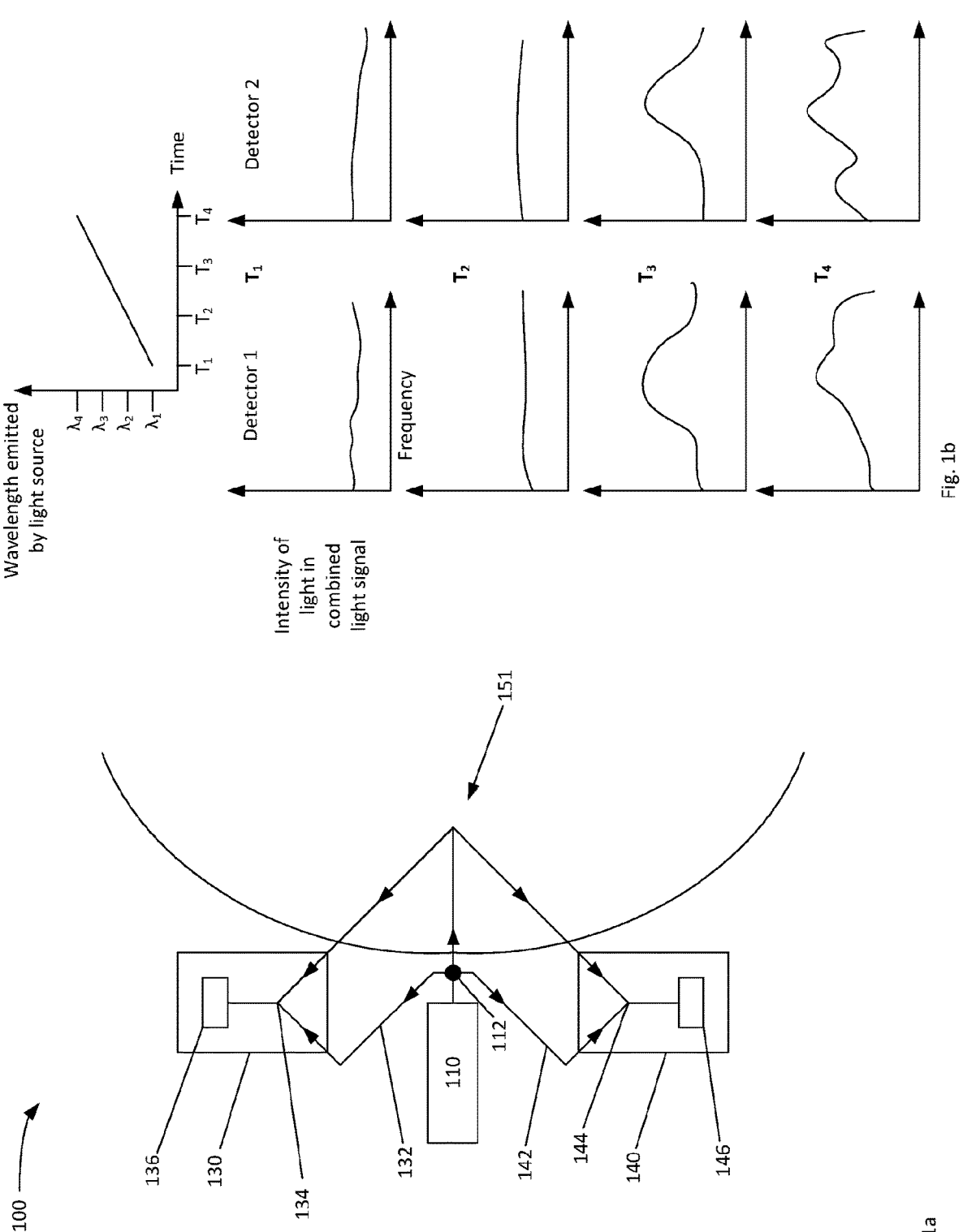
FIG. 1a is a schematic diagram of an exemplary EROS system.
FIG. 1b shows a series of graphs to illustrate an exemplary mode of operation of the EROS system of FIG. 1b for neuroimaging and analysis.

Embodiments of the present disclosure are directed to an event related optical signal ('EROS') system in which each light source is connected to a plurality of different detectors. Light from the light source is coherent and wavelength-swept so that coherent light is emitted from the light source at a plurality of different frequencies during one wavelength sweep. Some of this wavelength swept light is directed towards the subject's brain tissue where scattering events occur, and some of the wavelength swept light is directed to each of the detectors. Each detector then combines reference light received from the light source with scattered light received from the subject's brain tissue. As the light is coherent, the scattered light will combine with the reference light at the detector to form light at one or more beat frequencies. A value for these beat frequencies will indicate a difference in time of flight between light travelling along a reference path to the detector and light travelling via the subject's brain tissue. This may thus provide an indication of time of flight, and thus penetration depth information, for the light travelling into the subject's brain tissue. By monitoring this, neural events may be detected. In examples, multiple light sources may be used, where each light source has a one-to-many relationship with the detectors, so that it provides reference light to each of a plurality of detectors.

Basic Principle of EROS System

EROS systems of the present disclosure may direct amplitude modulated light to regions of the subject's brain tissue. Light signals caused by scattering of this light from the subject's brain tissue can then be detected by one or more detectors. The detectors are configured to detect one or more beat frequencies for scattered light received from the subject's brain tissue and reference light received from the light source. The resulting beat frequencies can be used to infer information about the scattering events which scattered the light back towards the detectors. For example, it may provide information about the optical path length from the source to the detector, which can be used to determine the depth in the tissue at which the scattering took place.

Light Sources

EROS systems of the present disclosure are arranged to direct light from one or more light sources towards a subject's brain tissue through the scalp and skull. These light sources will typically be positioned on the subject's scalp. The light sources provide coherent light (e.g. light which is self-coherent to enable beat frequencies to be generated between scattered and reference light from that light source). The coherent light from the one or more light sources is directed towards the subject's brain tissue so that it may pass through their scalp, skull and into their brain tissue. The coherent light from the light sources will be wavelength-swept so that it emits light at a plurality of different wavelengths during one wavelength sweep. It is to be appreciated that the penetration depth of this light may vary depending on a number of factors, such as the wavelength of the light, as well as material properties (e.g. density) of the medium through which the light is passing. Typically, light used in EROS systems of the present disclosure has near-infrared (NIR) wavelengths (e.g. 800 to 2500 nm). At these wavelengths, it can be expected that at least some of the light emitted from the light source will pass into the brain tissue of the subject (i.e. it will not all be blocked by the scalp/skull), and also some of the light will penetrate more deeply into the brain tissue to enable information to be obtained from a greater volume of brain tissue.

Optical Paths of Photons Directed Towards the Subject's Brain Tissue

As light from the one or more light sources passes through the subject's scalp, skull and/or brain tissue, light scattering events will occur as the light interacts with the medium through which it is travelling. It will be appreciated that there may be a plurality of different causes for a scattering event to occur, and the causes for these different scattering events to occur may also depend on properties of the light and/or the medium through which it is travelling. As a consequence of a scattering event, the light will change direction. Photons of light entering the brain tissue will diffuse, moving in random walks due to optical scattering until they are either absorbed or exit the brain tissue. The random nature of this diffusion means that although individual scattered photons have unpredictable paths, bulk photon movements can be accurately understood probabilistically.

The paths followed by masses of photons launched into the brain tissue from one light source and scattered back out onto a photodetector are well understood probabilistically. On average, the trajectories for photons from source to detector are arc-shaped, e.g. a plot of the different trajectories may have a banana shape.

Detectors, and the Spatial Arrangement of the Detectors Relative to the Light Sources The scattering of light within brain tissue and towards a detector will be referred to as 'back scattering of light'. EROS systems of the present disclosure may utilise one or more light detectors, such as interferometers, to measure this backscattered light. It will be appreciated that back scattered light will not always travel directly back towards any given location on the scalp, but instead, this light may travel in one of a plurality of different directions (e.g. back scattered light from one light source may be detected at a plurality of different locations on the subject's scalp). Light may be scattered a plurality of times before it reaches a detector. The depth reached by photons emitted from the source and picked up by the detector will be proportional to the distance between the source and detector. For example, short source-detector distances typically cover shallow tissue depths, whereas longer source-detector distances contain photons which travel deeper into the brain tissue. Embodiments of the present disclosure may utilise a plurality of source-detector pairs, each pair being spatially arranged to be associated with a selected depth of light penetration into the subject's brain.

Some of the back scattered light signals may carry information about activity occurring within the brain. The detectors may be operable to determine one or more properties of the back scattered light which they detect. The system may be configured to determine an indication of beat frequencies present in the light incident on the detector. In particular, such information about beat frequencies may be used to identify a time of flight ('TOF') for photons. Information about beat frequencies in the detected light may be used to provide an indication of the temporal offset of that scattered light as compared to the reference light which reached the detector along a path of known length. The resulting beat frequency for this scattered and reference light will provide an indication of the distance that photon has travelled to get from the source to detector (e.g. its optical path length). EROS systems of the present disclosure may utilise probabilistic models to estimate the photon path from source to detector, and/or the penetration depth of that photon within the brain tissue.

Neuroimaging and Analysis Based on Detected Signals

EROS systems of the present disclosure may be configured to detect an indication of fast optical signals ('FOS') occurring in the subject's brain tissue. These fast optical signals relate to neural activity, such activity can cause changes in optical scattering properties of the brain tissue in which that activity occurs. As such, scattering properties of light in brain tissue will vary concurrently with neural activity in that brain tissue, and so an indication of the neural activity occurring may be obtained based on information contained within scattered light signals measured by detectors. The physiological mechanisms responsible for such fast optical signals comprise cell swelling and membrane conformation changes. These changes may occur during the transfer of ions and water that happen during electrical neuronal events such as action potentials in the brain.

As a result of the fast optical signals occurring (or not occurring), different regions within the brain tissue will cause light scattering events at different rates. For example, when a region of the brain is active (e.g. when fast optical signals are being transmitted through that region of the brain), the activity in that region will lead to a different number and/or type of scattering events occurring, as compared to a region which is dormant (e.g. when no, or not many, fast optical signals are being transmitted through that region of the brain). This will be evident in the measured beat frequencies (time of flight information), as either a change in beat frequency will indicate an event occurring (e.g. which caused the scattering to occur), or an absolute value of the beat frequency itself will indicate a depth at which an event (e.g. a scattering) occurred.

Temporal Monitoring/Temporal Neuroimaging and Analysis

EROS systems of the present disclosure are configured to repeatedly (e.g. continuously) pass photons from the one or more light sources through intervening brain tissue to detectors of the system. By monitoring properties of the back scattered light received at the one or more detectors, systems of the present disclosure may determine whether any neural events are occurring (e.g. whether the detected signals correspond to regions of the brain through which fast optical signals are being transmitted). For example, neural activity in a volume of brain tissue may be inferred based on a change in the rate of scattering of light associated with that volume of brain tissue (e.g. light which has passed through that volume of brain tissue). EROS systems of the present disclosure may utilise a plurality of different detectors arranged to enable activity in different regions of the brain to be monitored at the same time. EROS systems of the present disclosure may utilise a plurality of different sources arranged to enable activity in different regions of the brain to be monitored at the same time.

By monitoring lots of detected photons, and having an estimate for their expected trajectories through the brain tissue, changes in neural activity may be identified based on measured beat frequencies at the detector. For example, where a detector pair initially receives photons having a consistent beat frequency (and thus consistent time of flight), and then photons are suddenly received having a different, e.g. lower, beat frequency (e.g. indicating a smaller time of flight), this may suggest that neural activity has occurred somewhere on that expected trajectory causing earlier scattering than expected. Based on this shorter time of flight, an indication of penetration depth for the scattering event may be determined, and this provides an indication of activity in a certain region of the brain tissue. Using these probabilistic methods, it is possible to filter out photons which did not reach the brain tissue, as these will have probabilistically travelled shorter paths from their source to a detector.

One specific example of an EROS system will now be described with reference to FIGS. 1a and 1b. Some alternative and/or additional features of EROS systems of the present disclosure will be described later with reference to FIGS. 2 and 3.

FIG. 1a shows an exemplary EROS system 100. The EROS system 100 includes a first light source 110 and a first output light splitter 112. The EROS system 100 also includes a first detector 130 and a second detector 140. The system 100 includes a first reference channel 132 and a second reference channel 142. The first detector 130 includes a first light combiner 134 and first signal processing circuitry 136, and the second detector 140 includes a second light combiner 144 and second signal processing circuitry 146. Also shown in FIG. 1 is a first scattering region 151.

The first light source 110 is connected to each of the detectors. The first light source 110 is connected to the first output light splitter 112. The first output light splitter 112 is connected to a sample channel which directs light from the light source to the subject's brain tissue. The first output light splitter 112 is also connected to each of the detectors. The first output light splitter 112 is connected to the two detectors via one or more reference channels. As shown, a respective reference channel connects the first output light splitter 112 to each of the detectors. The first reference channel 132 connects the first output light splitter 112 to the first detector 130, and the first reference channel 132 connects the second output light splitter to the second detector 140.

The first detector 130 comprises a first input port and a second input port. The first input port of the first detector 130 is located adjacent to the subject's head to receive scattered light from their brain tissue. The second input port of the first detector 130 is connected to the first reference channel 132. The first light combiner 134 is arranged at a connection between the first input port and the second input port. The first light combiner 134 is connected to the first signal processing circuitry 136 so that an output (e.g. combined light) from the first light combiner 134 is provided as an input to the first signal processing circuitry 136.

The second detector 140 comprises a first input port and a second input port. The first input port of the second detector 140 is located adjacent to the subject's head to receive scattered light from their brain tissue. The second input port of the second detector 140 is connected to the first reference channel 132. The second light combiner 144 is arranged at a connection between the first input port and the second input port. The second light combiner 144 is connected to the second signal processing circuitry 146 so that an output (e.g. combined light) from the second light combiner 144 is provided as an input to the second signal processing circuitry 146.

The first light source 110 is configured to emit wavelength swept emission of coherent light. The first light source 110 is configured to produce a series of pulses of laser light. During each pulse, the wavelength of the light is "swept" through a range, in the manner of a chirped pulse. Thus, during each pulse the laser sequentially outputs each of a plurality of different wavelengths of light. This series of chirped pulses may be contiguous (e.g. the inter-pulse interval may be zero) so that the laser light comprises a sequence of successive wavelength sweeps. The first light source 110 may comprise a laser, such as a distributed feedback laser. It is to be appreciated in the context of the present disclosure that light sources need not provide a continuous sweeping for emission of coherent light, and instead may emit light at different wavelengths in discrete time intervals, e.g. at a first wavelength for a first time period, then at a second wavelength for a second time period etc.

The first light source 110 may be configured to provide fast wavelength tuning. For example, the first light source 110 may be configured to provide wavelength tuning at or above 1000 nm/s. The first light source 110 may be configured to provide high laser coherence, e.g. equivalent to a line-width at 100 MHz or less. The first light source 110 may be configured to provide power at more than 1 mW, e.g. at between 1 and 100 mW. The light source 110 may be configured to provide a sweep rate at 5 kHz or more, e.g. 10 kHz or more, e.g. 15 kHz or more, e.g. 20 kHz or more. For example, the light source may be configured to provide a tuning rate 20000 nm/s or above. For example, the first light source may comprise any of a distributed feedback laser, a distributed Bragg-reflector laser, a Fourier domain mode locked laser and/or a micro-electromechanical vertical cavity surface emitting laser (e.g. MEMS-VCSEL laser).

The first light source 110 is configured to generate and emit coherent light so that scattered light from the first light source 110 may combine, at a detector, with reference light from that light source to provide light at one or more beat frequencies (e.g. corresponding to a difference in wavelength between the reference light and the scattered light at the detector). The first light source 110 is arranged on or proximal to the subject's scalp for directing the coherent light towards their brain tissue. The first light source 110 is configured to sweep through a selected wavelength range. For example, the first light source 110 may be configured to sweep in optical frequency over a range of 50 GHZ. For example, this may enable the light source to emit modulated light at a plurality of different wavelengths between e.g. 829.94 nm and 830.06 nm when centred on 830 nm for example or between 1309.857 nm and 1310.143 nm when centred on 1310 nm for example The laser may sweep unidirectionally (e.g. only increasing or decreasing in wavelength during one wavelength sweep), or it may sweep bidirectionally (e.g. both increasing and decreasing in wavelength during one wavelength sweep). For example, the first light source 110 may be configured to sweep through a wavelength range of at least 0.025 nm, such as at least 0.05 nm, such as at least 0.075 nm, such as at least 0.1 nm, such as at least 0.11 nm (e.g. about a wavelength on which it is centred).

The first light source 110 is configured to wavelength sweep according to a selected pattern for the sweeping. For example, the first light source 110 may sweep through a selected range of wavelengths of light and/or the first light source 110 may sweep through wavelengths of light according to a selected sweep profile (e.g. linear increasing, sinusoid, triangular etc.). For example, the light source may sweep according to a selected sweeping rate, or a selected total sweeping time. The first light source 110 is configured to wavelength sweep light so that during one wavelength sweep, light will be directed to the subject's brain tissue and to the detectors at each of a plurality of different frequencies. The wavelength of light emitted by the light source will vary over time, e.g. so that an indication of the time of emission for the light may be obtained based on a wavelength of the light. For example, the first light source 110 may provide chirped emission of light. The wavelength of light emitted by the light source will vary according to a fixed pattern. The fixed pattern for wavelength varying will be known, e.g. the system may comprise a data store which stores an indication of this pattern, or a property of the light source (such as sweep rate) which may enable this fixed pattern to be determined.

The first output light splitter 112 is configured to direct split light from the first light source 110 to each of a plurality of different locations. The first output light splitter 112 is arranged to deliver some of the light from the first light source 110 towards the subject's brain tissue, as well as some of the light to the first detector 130 (via the first reference channel 132) and some of the light to the second detector 140 (via the first reference channel 132). The first output light splitter 112 may be arranged to direct a majority of the light from the first light source 110 towards the subject's brain tissue. It is to be appreciated in the context of the present disclosure that the first output light splitter 112 need not split three ways—instead the first output light splitter 112 may split light between a sample channel (for directing light to the subject's brain tissue) and a reference channel (for directing light to the detectors), and a further component such as a splitter may be arranged to deliver the reference light to each individual detector. The first output light splitter 112 may split light in more than three ways, e.g. to a plurality of different detectors.

Light from the first light source 110 is arranged to be delivered towards the subject's brain tissue. Light from the first light source 110 is also arranged to be delivered to each of the detectors as reference light. The light delivered to the subject's brain tissue will scatter, such as in the first scattering region 151. The first and second detectors are arranged to be located in regions where the scattered light may be detected. The detectors will typically be placed on, or proximal to, the subject's head. The first and second detector may be arranged at different distances away from the first light source 110 on the subject's head.

Each of the first and second detector are arranged so that scattered light from the subject's brain tissue will be delivered to the first input port of the detector. Each of the first and second detector are arranged so that reference light will be delivered to the second input port of the detector. Reference light will be delivered to the first detector 130 via the first reference channel 132, and reference light will be delivered to the second detector 140 via the first reference channel 132.

The system 100 is arranged so that an average, or expected, optical path length for light travelling from the first light source 110 to each detector via the subject's brain tissue will be different to the optical path length for light travelling from the first light source 110 to said detector via the respective reference channel. In other words, the system 100 is arranged so that scattered light which was emitted from the first light source 110 and scattered with the subject's brain tissue will take a different amount of time to reach a detector than the reference light which travelled to the detector via a corresponding reference channel. Each of the first and second reference channel is of a selected length, wherein that selected length is selected to be less than an expected optical path length via the subject's brain tissue. For example, each reference channel is arranged to be of a shorter length than the optical path length via the patient's brain tissue. One of the reference channels may have a shorter path length than the other. At least one reference path distance may be selected to be nearly equal to the sample path length, e.g. to provide lower beat frequencies. Another one of the reference path lengths may be different, e.g. shorter than this reference path distance.

Each of the detectors is arranged to receive both scattered light and reference light and to combine the two using their respective light combiner. For example, each of the detectors may comprise an interferometer assembly configured to combine the reference light and the scattered light to obtain an interference pattern. The first light source 110 is configured to emit coherent light and so the interference pattern for coherent light from the first light source 110 (as obtained at each detector) may comprise a combined signal having components at beat (or intermediate/difference) frequencies corresponding to the difference in frequency between the scattered light and the reference light. Each light combiner is arranged to combine the light, and to provide said combined light (which may include one or more components corresponding to beat frequencies) to the signal processing circuitry. Each of the detectors may comprise a square law detector. For example, each detector may be configured to create an interference pattern based on the difference in optical frequencies, e.g. wherein the intensity or power detected is proportional to the square of the incident electric field. Such detectors may comprise photodiodes, avalanche photodiodes and/or fast linescan cameras, streak cameras and fast CCD or CMOS sensors. The detector may be a high bandwidth detector. For example, the detector may be configured to resolve interference fringes at 100 Mhz or more, such as up to 1 GHz. The detector may comprise a single speckle detector. For example, optical fibers used in the detector may be single mode. If a multi-mode detector is used, then the detector may comprise an array of square-law detectors, such as a photodiode array. The detector may also comprise a balanced detector array. For example, the balanced detector array may be configured so that the reference light and the scattered light are combined and split (e.g. evenly) onto a pair of out-of-phase detectors such as with a 4-port (2-in, 2-out 50:50 ratio) fiber coupler or a beamsplitter cube. A balanced detector may enhance signal to noise of the detected signal by rejecting incoherent portions of the signal.

The scattered light travelling from the light source to each detector via the subject's brain tissue will take a different amount of time to arrive at said detector compared to the reference light travelling along the reference channel. This time difference will mean that the reference light which is combined with the scattered light at any one time will have been emitted after the scattered light. Due to the wavelength sweeping of the first light source 110, the reference light which is combined with the scattered light may have been emitted at a different wavelength, and thus there may be a difference in wavelength between the scattered and reference light (thus giving rise to generation of a beat frequency).

The system 100 is arranged so that the wavelength of reference light received at a detector at a given time will be different to wavelengths of scattered light expected to be received at that given time. The system 100 is arranged so that the light source will provide reference light to each of the detectors at a wavelength which is expected to be different to wavelengths of scattered light each detector will receive through their respective first port. The system 100 is arranged so that each detector is configured to combine scattered light with reference light to provide combined light comprising one or more components corresponding to beat frequencies between received scattered light and the reference light.

It is to be appreciated in the context of the present disclosure that light from the first light source 110 may take a variable amount of time to reach the detector via the subject's brain tissue, as the optical path length (and thus time of flight) may vary depending on the number and nature of scattering events which occur to that light. Therefore, each detector may be receiving scattered light at a plurality of different wavelengths (as, at any one time, scattered light received at the detector may have been emitted from the first light source 110 at a plurality of different times, and thus at different wavelengths). Each detector may be arranged to combine reference and scattered light to provide a combined light signal comprising a plurality of different beat frequency components. As described in more detail below (e.g. with reference to FIG. 1*b*), the system 100 may be configured to provide neuroimaging and analysis based on an indication of at least one of: (i) a value for beat frequencies identified in the combined signal, (ii) a change in one or more of the beat frequencies identified in the combined signal, (iii) an intensity of one or more of the identified beat frequencies, (iv) a change in the intensity of the identified beat frequencies, (v) an average frequency for identified beat frequencies, and (vi) an average intensity of the identified beat frequencies.

In operation, the first light source 110 emits coherent light for one wavelength sweep. During this wavelength sweep, the first light source 110 emits light at each of a plurality of different wavelengths. In this example, the first light source 110 emits light so that the wavelength increases throughout the wavelength sweep (e.g. a down chirp). An example of this is shown in the top graph in FIG. 1*b*, where the wavelength of light emitted by the first light source 110 increases from a wavelength $\lambda_1$ at a time $T_1$ to a wavelength $\lambda_2$ at a time $T_4$. In the example shown in FIG. 1$b$, the increase in wavelength is linear over time.

This wavelength-swept light is split between being directed to the subject's brain tissue and the detectors. The majority of the light is directed to the subject's brain tissue, where scattering events occur until this scattered light reaches one of the detectors (or is attenuated/travels elsewhere). A portion of the light is directed to each of the detectors along a corresponding reference channel. Scattered light from the subject's brain tissue is received at the first port of a detector, and reference light is received at the second port of a detector. While detecting, each detector will receive light at both its first and second ports. Some of the light received at the first port may comprise scattered light which was emitted by the first light source 110 and which has scattered in the subject's brain tissue and been directed to the detector. The light received at the second port comprises reference light received from the first light source 110.

The light from the first and second ports are then combined at each detector, e.g. as they would be in an interferometer. The first light combiner 134 is configured to combine the scattered light with the reference light, e.g. the first detector 130 and/or the first light combiner 134 may comprise an interferometer. For example, each detector may be an interferometer, wherein each light combiner is a linear wavelength insensitive beam combiner, such as a 50:50 fiber combiner or beam splitter cube. The first light combiner 134 is configured to combine the scattered light with the reference light so that an interference pattern is generated and this interference pattern is contained in the combined signal output from the first light combiner 134. The first light combiner 134 is configured so that at any one time, the reference light it has received from the first light source 110 will be combined with the light it has detected from the subject's brain tissue (which may include some scattered light which originated from the first light source 110). The first light combiner 134 is configured to combine this reference light with this scattered light to enable one or more beat frequencies to be generated which correspond to the difference frequencies between reference light and scattered light from the first light source 110.

It will be appreciated in the context of the present disclosure that, as the reference light is coherent with the scattered light (they were both emitted by the same first light source 110), the first light source combiner 134 will combine the reference and scattered light to produce light at one or more beat frequencies (which correspond to the difference in wavelength between the reference and scattered light). This light at beat frequencies in the combined signal may provide an indication of path length difference between the scattered light and the reference light. The first light source 110 is arranged to sweep through wavelengths, and to provide some of its emitted light as reference light to the detectors. It will take some time for this reference light to reach the detector (due to the optical path length for light travelling from the light source 110 to the detector). As such, the wavelength of the reference light received at a detector will correspond to a wavelength emitted by the first light source 110 at a time in the past. Likewise, due to the optical path length for light directed to the subject's brain tissue, the wavelength of the scattered light received at the detector will correspond to a wavelength emitted by the first light source 110 at a time in the past.

The system 100 is arranged so that an expected (or average) optical path length for the scattered light from the light source 110 to the detector will be different to the optical path length for the reference light from the light source 110 to the detector. Due to the wavelength sweeping of the first light source 110, the scattered light will be at a different wavelength to the reference light. The system 100 is arranged so that the optical path length for the reference light will be shorter. Therefore, the wavelength of the reference light received at the detector will correspond to a wavelength of light more recently emitted by the first light source 110 than the wavelength of the scattered light. Also, as photons of light emitted from the first light source 110 will travel different optical path lengths before reaching the detector (due to the random nature of scattering events), the scattered light received at the detector will comprise components at different wavelengths (corresponding to the different times at which the light was emitted from the first light source 110). For scattered light which travelled further before reaching the detector, its wavelength will correspond to wavelength of light emitted longer ago than scattered light which travelled less far.

In this example, the wavelength of light emitted by the first light source 110 will increase over time during one wavelength sweep. It follows that reference light received at a detector will also increase in wavelength over time. The wavelength of scattered light will depend on the optical path length the light has travelled to the detector. For a given optical path length, the scattered light will increase in wavelength over time. However, it will be appreciated that scattered light may travel different optical path lengths before reaching the detector. The wavelength of the scattered light may thus indicate the optical path length that the light has travelled, as it will indicate how long ago that light was emitted (based on its wavelength). Each light combiner is configured to combine the scattered and reference light to provide a combined light signal where that combined light signal includes components at one or more beat frequencies for combination of scattered and reference light. The light processing circuitry is configured to process such combined signals to identify data pertaining to the difference in wavelength between the scattered and reference light, e.g. to obtain an indication of a difference in optical path length between the two, and thus an indication of the optical path length travelled by the scattered light (as the reference light will travel a fixed optical path length).

The combined light provided to the signal processing circuitry will include components at one or more of a plurality of different beat frequencies. The particular beat frequencies observed will correspond to the variations in time of flight for scattered light, as the reference light will take a fixed amount of time to reach the detector. Therefore, based on beat frequencies in the combined light, information relating to scattering events occurring in the brain may be obtained. It is to be appreciated in the context of the present disclosure, that large amounts of light may be directed towards the subject's brain tissue (i.e. many photons), and there may be great variety in the scattering events occurring within the subject's brain tissue. As such, lots of scattered light may be received at the detector, and this may include components at many different wavelengths emitted by the first light source 110 (and thus a large number of beat frequencies). The combined signal will therefore contain a number of different beat frequencies, and these may provide a wealth of information about scattering events occurring in the subject's brain tissue. Likewise, any changes in these beat frequencies (or their amplitudes) may provide information about scattering events.

The combined signals may be processed by the signal processing circuitry to provide neuroimaging and analysis.

In particular, based on the combined signal, information relating to scattering events may be inferred, such as any change in neural activity, a depth at which neural activity occurs and/or an indication of a type of neural activity occurring (and an associated region in which that activity is occurring). However, it is to be appreciated in the context of the present disclosure that the precise method of processing this combined signal to infer properties relating to neural activity should not be considered limiting. For example, beat frequencies and/or time of flight data may be explicitly determined, and properties inferred based on this, or this information may never explicitly be calculated, and instead information may be obtained based purely on changes between subsequent measurements, or averages over time. In some examples, each combined signal may be provided as the input to a machine learning element configured to infer one or more properties about neural activity, or each combined signal may be stored in a data store for later processing.

To illustrate one example way of processing the combined signal to infer neural activity, reference will now be made to FIG. 1b which shows a series of graphs to illustrate one way of inferring information about neural activity from the combined signal.

FIG. 1b shows a first graph of the wavelength sweeping of the first light source 110. In this graph, the wavelength increases during one wavelength sweep. Four times $T_1$, $T_2$, $T_3$ and $T_4$ are shown, as are the corresponding wavelengths $\lambda_1$, $\lambda_2$, $\lambda_3$ and $\lambda_4$. The remaining 8 graphs show an indication of an observed intensity spectrum for different frequencies of light in the combined light signals from the detectors. The four graphs in the left column relate to the combined light signal for the first detector 130, and the four graphs in the right column relate to the combined light signal for the second detector 140. Each row corresponds to a time $T_1$, $T_2$, $T_3$ and then $T_4$. For the purposes of this illustration, it is taken that the first wavelength swept light source only starts emitting light at $T_1$. At times $T_1$ and $T_2$, the observed intensity spectrum is relatively featureless over the frequency range shown. This may indicate that the majority of the light received at the first input port of the two detectors corresponds to background noise, and that no signal is readily discernible from this noise. In this example, it may be inferred from this lack of signal that the majority of the light emitted from the first light source 110 to the subject's brain tissue has not yet scattered and reached either of the two detectors.

At time $T_3$, the observed intensity spectrum for each detector contains more features. As can be seen, both a roughly Gaussian (e.g. bell-shaped) with some sort of intensity peak, and a spread either side of the peak where the intensity is raised as compared to the background. Based on this distribution it may be inferred that reference light and scattered light are combining to provide light at certain beat frequencies. Notably, this includes frequencies at, or close to, the frequency at which the intensity peak occurs. This beat frequency, or this range of beat frequencies surround this beat frequency, may enable an indication of time of flight to be determined for that scattered light. Based on the observed beat frequencies, a wavelength difference between the relevant scattered and reference light may be determined (the beat frequency will correspond to this wavelength difference). Based on properties of the wavelength sweep, such as sweep rate or other timing data indicating what wavelength of light was emitted at each time, a timing offset may be determined between the time it took for the reference light to reach the detector as compared to the time it took for the scattered light to reach the detector. This may therefore provide an indication of optical path length/time of flight differences between the scattered and reference light.

The indication of optical path length difference/time of flight difference may enable a penetration depth into the brain tissue to be estimated. This may be done using statistical methods or based on empirical data. Therefore, the observed beat frequencies from the combined signal may enable an indication of the penetration depth at which the scattering events occurred to be determined. Systems and methods of the present disclosure may not ever actually calculate this information, as instead information may be obtained based on monitoring how the graphs change over time. For example, each subsequent graph over time may show a similar bell curve to that shown at $T_3$, and this may effectively represent background scattering information. For example, background scattering may provide an indication of the expected time of flight/optical path length distribution for light scattering in the brain tissue in the absence of any particular neural event occurring, or it may also represent typical neural events occurring. This may therefore represent a baseline against which changes may be detected, and it may be these changes from which neural information is inferred. For example, a change to the shape of the distribution, or a change in values for the distribution over time may indicate that neural events are occurring.

At time $T_4$, the distribution has changed slightly to illustrate that e.g. different neural events may have occurred. For both the first and second detector, a similar peak to that at $T_3$ occurs, and there is a relatively bell-shaped spread around that peak (at least partially). However, additional peaks are also present. This is particularly evident in the graph for the second detector 140, which shows a peak at both a higher and a lower frequency than the main peak. Based on this distribution it may be inferred that some form of neural activity has prompted an intensity peak in certain beat frequency ranges. For example, for the lower frequency peak, it may be inferred that a neural event occurring close to the surface has occurred, and as such photons are travelling less far before scattering to the detector (and thus the resulting beat frequencies are lower, as there is less difference in time of light between the scattered and reference light. Similar properties may be inferred from the higher frequency peak, e.g. that a disproportionately large number of photons are travelling for a longer time period than expected, thus giving rise to greater beat frequencies.

However, as set out above, it is to be appreciated that this description of inferring neural activity is not to be considered limiting, and is instead to illustrate the functionality present based on the obtained combined light signal at each detector. The EROS systems described herein may enable a one-to-many relationship between each source and a plurality of detectors, so that each of the many detectors may be arranged to receive the relevant reference light for the source, and to processing light received at that detector corresponding to that light source.

The data obtained from the combined light signals may be processed in a number of different ways. For example, the system 100 may be configured to batch data for a plurality of wavelength sweeps into one batch which is analysed, e.g. data for a selected time window may be averaged, and only that average used. As one example, of this, the first light source 110 may sweep at e.g. 200 kHz. This may enable data from 200 sweeps to be used together (e.g. the obtained data may be averaged over this period) to provide a 1 ms window of data. Neural activity, or changes in neural activity, may be inferred based on each 1 ms window of data, rather than that from any individual instance in time.

Alternative and/or additional features of exemplary EROS systems of the present disclosure will now be described with reference to FIG. 2.

Figure 2:
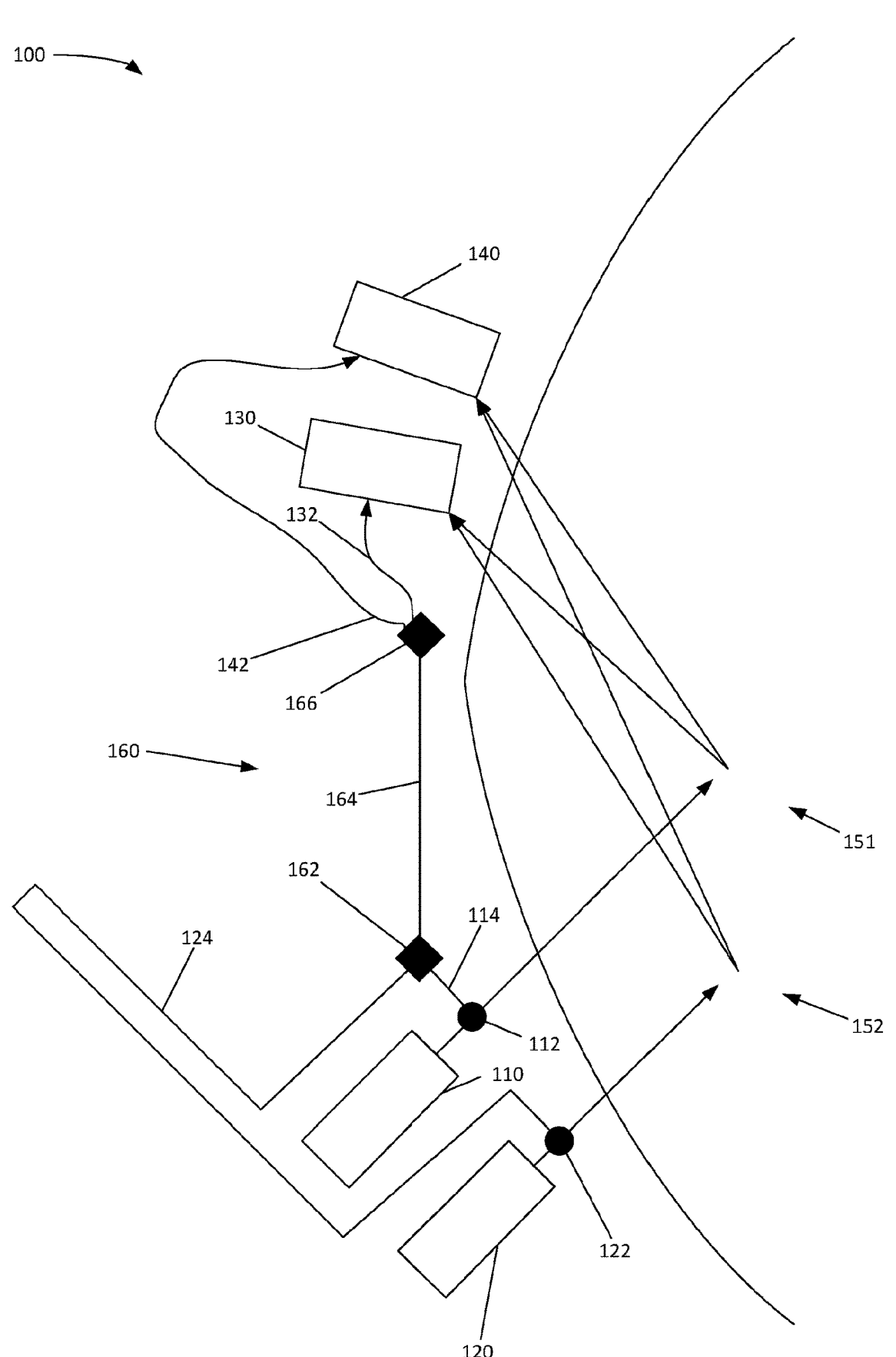
FIG. 2 is a schematic diagram of an exemplary EROS system.

FIG. 2 shows an exemplary EROS system 100. The EROS system 100 of FIG. 2 is similar to that of FIG. 1a, and so components of the system 100 which have previously been described with reference to FIG. 1a will not be described again.

In addition to the features shown in FIG. 1a, the EROS system 100 of FIG. 2 includes a second light source 120 and a signal combining assembly 160. The second light source 120 includes a second output light splitter 122. The signal combining assembly 160 comprises a carrier channel 164. The signal combining assembly 160 also includes a carrier channel combiner 162 and a carrier channel separator 166. Also shown is a first connector 114 for the first light source 110 and a second connector 124 for the second light source 120. FIG. 2 also shows a second scattering region 152.

Each of the first and second light sources may be connected to the signal combining assembly 160. The first output light splitter 112 is connected to the carrier channel combiner 162 via the first connector 114. The second output light splitter 122 is connected to the carrier channel combiner 162 via the second connector 124. The first connector 114 may be of a different length to the second connector 124. As shown in FIG. 2, the second connector 124 may be longer than the first connector 114. The carrier channel combiner 162 may connect both the first and second connector to the carrier channel 164. The carrier channel separator 166 may connect the carrier channel 164 to each of the first and second reference channel.

The second light source 120 may be similar to the first light source 110, as described above, and so shall not be described again. The system 100 may be arranged so that reference light from the first and second light source has to travel a different optical path length to the carrier channel combiner 162. The system 100 may be arranged so that the reference light from the second light source 120 has to travel an additional distance to reach each detector than the reference light from the first light source 110. For example, the additional distance may be more than a selected distance. The selected distance may be selected so that there is no, or minimal, spectral overlap in the resulting beat frequencies for the first and second reference light at the first detector 130. For example, the system 100 may be arranged so that the optical path length difference between: (i) the first light source 110 and the first detector 130, and (ii) the second light source 120 and the first detector 130, may be large enough that the resulting beat frequencies obtained at the first light source 110 (e.g. scattered/reference light from first light source 110, and scattered/reference light from second light source 120) have no, or minimal, spectral overlap. The resulting beat frequencies from the two different light sources in a combined light signal at the first detector 130 may therefore not overlap.

The carrier channel combiner 162 may be configured to combine the reference light from the first light source 110 and the reference light from the second light source 120 onto the carrier channel 164. The carrier channel combiner 162 may be configured to combine the two reference light signals onto the carrier channel 164 so that both reference lights signals may be transmitted towards the detectors together. For example, the carrier channel combiner 162 may comprise a multiplexer, a grating and/or a fiber splitter, e.g. a 1×N fiber splitter. The carrier channel 164 may transmit reference light from each of the light sources towards the detector. The carrier channel separator 166 may be configured to provide the reference light signals from the carrier channel 164 to each of the first and second reference channels.

The carrier channel separator 166 may be configured to distribute the reference signals evenly between each of the different reference channels to the detectors. The carrier channel separator 166 may be configured to provide both the reference light from the first light source 110 and the reference light from the second light source 120 onto each reference channel. For example, the second input port of each detector may be arranged to receive reference light from both the first and second detectors. The beam combiner may therefore be configured to combine scattered light received which originated from both of the light sources and reference light from both of the light sources. The carrier channel separator 166 may comprise any of a demultiplexer, a fiber splitter such as a 1×N fiber splitter. The carrier channel separator 166 may be configured to distribute reference light to each of the reference channels in a wavelength agnostic manner. The carrier channel separator 166 may be configured to distribute reference light from each light source to each reference channel.

The detectors may be arranged in a similar manner to that described above for the first detector 130, and shall not be described again in detail. However, it is to be appreciated that the first input port for each detector may be arranged to receive light from the subject's brain tissue. This received light may comprise scattered light which originated from the first light and source, and scattered light which originated from the second light source 120. The second port of each detector may be configured to receive reference light from each of the light sources. The light combiner may be configured to combine one or more sources of reference light with one or more types of scattered light. The combined signal may therefore comprise beat frequencies for scattered/reference light originating from the first light source 110, and scattered/reference light originating from the second light source 120. Signal processing circuitry for each of the detectors may therefore process and obtain neural activity information from light originating from multiple different light sources.

The first and second light source may be arranged to be incoherent with one another. Light from the different light sources may not interfere to provide light at one or more beat frequencies. Alternatively, or additionally, the system 100 may be configured to provide time-multiplexed operation of the different light sources so that at any one time, light is only being received at the detectors which originated from one light source.

Some further alternative and/or additional features of exemplary EROS systems of the present disclosure will now be described with reference to FIG. 3.

Figure 3:
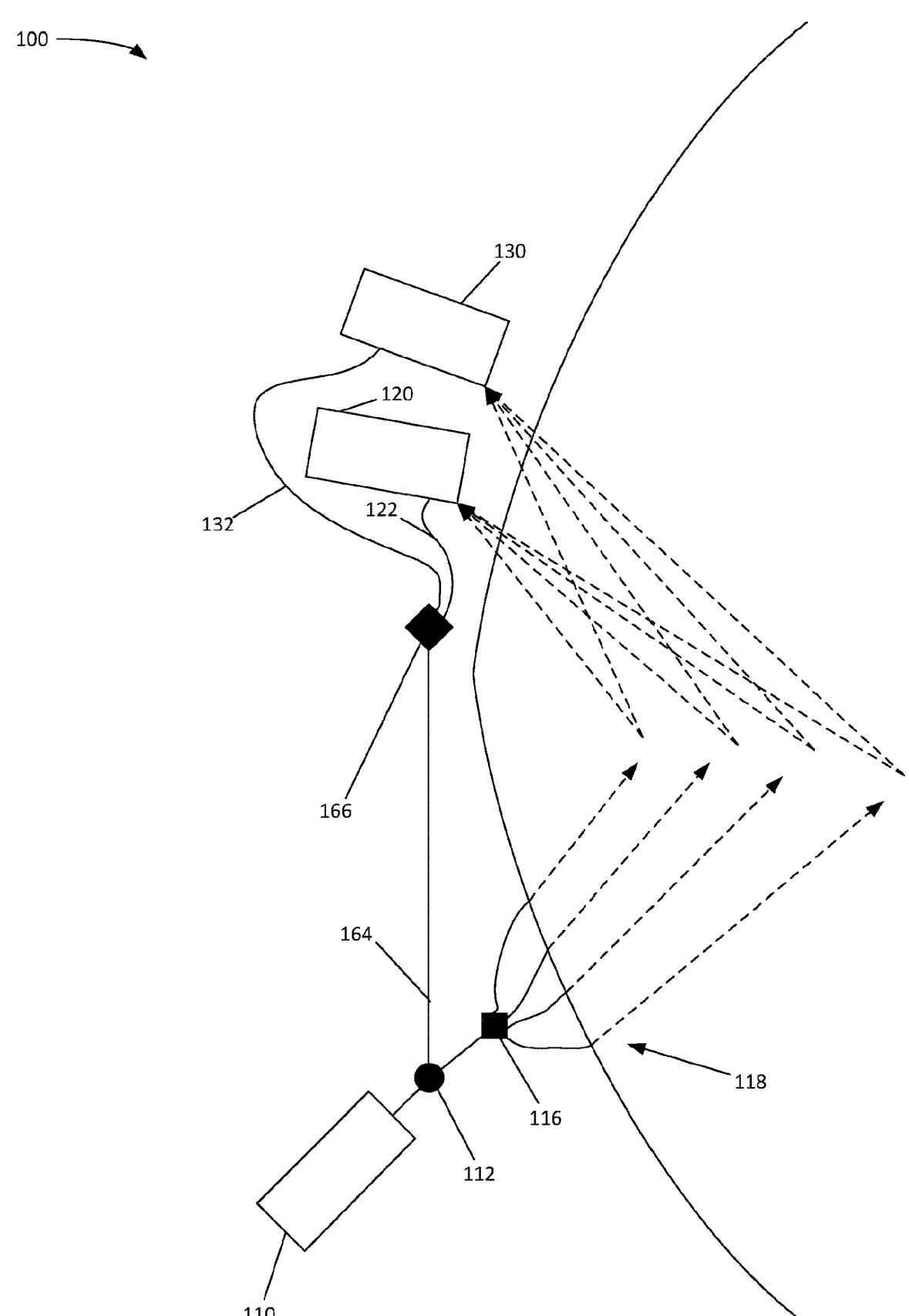
FIG. 3 is a schematic diagram of an exemplary EROS system.

FIG. 3 shows an exemplary EROS system 100. The EROS system 100 of FIG. 3 is similar to that of FIGS. 1a and 2, and so components of the system 100 which have previously been described with reference to FIGS. 1a and 2 will not be described again.

In addition to the features shown in FIG. 1a, the EROS system 100 of FIG. 3 includes an optical switch 116 and a plurality of signal delivery channels 118. The system 100 of FIG. 3 also includes a carrier channel 164 and a carrier channel separator 166 (as also shown in FIG. 2).

The system 100 of FIG. 3 is arranged to selectively direct light from one light source towards a plurality of different locations in the subject's brain tissue. The optical switch 116 is configured to selectively deliver light from the first light source 110 to one of the plurality of signal delivery channels 118 at a time. For example, the optical switch 116 may be configured so that a plurality of wavelength sweeps of light are delivered to a signal delivery channel before switching to deliver light to a different signal delivery channel. The system 100 may be configured so that reference light from the light source is provided to each detector and to only one of the signal delivery channels at a time. Operation of the system 100 may otherwise be the same as for systems described herein.

It is to be appreciated that the exemplary EROS systems described herein need not be considered limiting. For example, in the example shown in FIG. 1b, the wavelength swept emission of light comprises emission of light where the wavelength increases for a selected time period at a fixed rate. However, additional or alternative sweeping patterns may be used for the wavelength swept emission of light. For example, during one wavelength sweep the wavelength may both increase for a period then decrease for a period, such as bidirectional linear sweep (which forms a triangular wave), or a continuously varying sweep such as a sinusoidal sweep. In these examples, the sweeps may be bidirectional, but in other examples, these profiles (e.g. triangular, sinusoidal) can be implemented with unidirectional sweeps. This may be advantageous as the laser properties can be different in the upward and downward directions, which has reduce complexity. For example, the triangular wave may be particularly advantageous, as it may potentially resolve doppler dynamics of tissue due to the sign change.

In examples described herein, reference channels form part of a connection for connecting reference light from different light sources to a plurality of different defenders. However, it is to be appreciated that the particular arrangements shown for connecting light from one light source to a plurality of different detectors need not be considered limiting. For example, each detector may have a direct connection to each light source (and vice versa), or one or more splitters may split light to enable light from one source to be directed to a plurality of different detectors.

EROS systems of the present disclosure may be provided as part of a system configured to be placed on a subject's head, such as a human (e.g. adult human). The system 100 may comprise attachment means to enable the system 100 to be attached to a subject's head. For example, the system 100 may comprise a membrane arranged to be affixed to the subject's head. Each reference channel may be connected to the membrane. The membrane may support the system 100 to provide a fixed frame of reference for each channel of the system 100, e.g. so that all parts of the system 100 would move together (with the membrane). Components of each detector may be provided on single integrated circuits. For example, for each detector, the first input port, the second input port and the light combiner may be provided on one integrated circuit.

It will be appreciated from the discussion above that the examples shown in the figures are merely exemplary, and include features which may be generalised, removed or replaced as described herein and as set out in the claims. With reference to the drawings in general, it will be appreciated that schematic functional block diagrams are used to indicate functionality of systems and apparatus described herein. In addition, the processing functionality may also be provided by devices which are supported by an electronic device. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some examples the function of one or more elements shown in the drawings may be integrated into a single functional unit.

As will be appreciated by the skilled reader in the context of the present disclosure, each of the examples described herein may be implemented in a variety of different ways. Any feature of any aspects of the disclosure may be combined with any of the other aspects of the disclosure. For example method aspects may be combined with apparatus aspects, and features described with reference to the operation of particular elements of apparatus may be provided in methods which do not use those particular types of apparatus. In addition, each of the features of each of the examples is intended to be separable from the features which it is described in combination with, unless it is expressly stated that some other feature is essential to its operation. Each of these separable features may of course be combined with any of the other features of the examples in which it is described, or with any of the other features or combination of features of any of the other examples described herein. Furthermore, equivalents and modifications not described above may also be employed without departing from the invention.

Certain features of the methods described herein may be implemented in hardware, and one or more functions of the apparatus may be implemented in method steps. It will also be appreciated in the context of the present disclosure that the methods described herein need not be performed in the order in which they are described, nor necessarily in the order in which they are depicted in the drawings. Accordingly, aspects of the disclosure which are described with reference to products or apparatus are also intended to be implemented as methods and vice versa. The methods described herein may be implemented in computer programs, or in hardware or in any combination thereof. Computer programs include software, middleware, firmware, and any combination thereof. Such programs may be provided as signals or network messages and may be recorded on computer readable media such as tangible computer readable media which may store the computer programs in non-transitory form. Hardware includes computers, hand-held devices, programmable processors, general purpose processors, application specific integrated circuits (ASICs), field programmable gate arrays (FPGAs), and arrays of logic gates.

Any controller described herein may be provided by any control apparatus such as a general purpose processor configured with a computer program product configured to program the processor to operate according to any one of the methods described herein. In addition, the functionality of the controller may be provided by an application specific integrated circuit, ASIC, or by a field programmable gate array, FPGA, or by a configuration of logic gates, or by any other control apparatus.

Other examples and variations of the disclosure will be apparent to the skilled addressee in the context of the present disclosure.

The invention claimed is:

1. A system for monitoring a subject's brain, the system comprising:

a first wavelength-swept light source configured to provide wavelength-swept emission of coherent light; and a plurality of light detectors;

wherein the first wavelength-swept light source is arranged to both: (i) deliver the light towards the subject's brain tissue to be scattered to the detectors, and (ii) deliver the light to each of the detectors via one or more reference channels;

wherein each of the light detectors comprises:

a first input port arranged to receive scattered light from the subject's brain tissue;

a second input port coupled to one of the reference channels to receive reference light from the first light source;

a light combiner connected to both the first input port and the second input port for combining the scattered light received from the subject's brain tissue with the reference light received from the reference channel to provide a combined light signal comprising a component at a beat frequency for the scattered and reference light; and signal processing circuitry configured to provide an indication of effects in the subject's brain tissue based on changes in a distribution of a plurality of components at different beat frequencies of the combined light signal.

2. The system of claim 1, wherein the system comprises a reference light splitter arranged to receive the reference light from the first light source to be delivered to each of the detectors.

3. The system of claim 2, wherein the reference light splitter is configured to split the reference light from the first light source between: (i) a first reference channel connected to the second input port of a first detector of the plurality of detectors, and (ii) a second reference channel connected to the second input port of a second detector of the plurality of detectors.

4. The system of claim 1, wherein first light source is configured to emit coherent light at each of a plurality of different wavelengths during one wavelength sweep; and wherein, for each wavelength of light emitted by the first light source, each detector is configured to combine said reference light received from the light source with the scattered light from the subject's brain to provide a combined light signal, so that a plurality of different combined light signals are obtained during one wavelength sweep.

5. The system of claim 4, wherein the signal processing circuitry of each detector is configured to provide the indication based on the plurality of obtained combined light signals.

6. The system of claim 5, wherein the system is configured to provide the indication based on an indication of a value of the beat frequencies in the obtained combined light signals and/or an indication of a change in value of the beat frequencies.

7. The system of claim 6, wherein the system is configured to provide the indication based on timing data for each of the different wavelengths emitted by the first light source, and wherein the timing data comprises an indication of a sweep rate of the light source.

8. The system of claim 1, wherein the system comprises a second wavelength-swept light source configured to provide wavelength-swept emission of coherent light; and wherein the second wavelength-swept light source is arranged to both: (i) deliver light towards the subject's brain tissue to be scattered to the detectors, and (ii) deliver reference light to each of the detectors via the one or more reference channels.

9. The system of claim 8, wherein for each of the light detectors, the light combiner is configured to combine the scattered light received from the subject's brain tissue with at least one of: (i) the reference light received from the first light source via the reference channel, and (ii) the reference light received from the second light source via the reference channel, to provide the combined light signal.

10. The system of claim 8, wherein the system is arranged so that reference light from the first light source travels less far to reach the detectors than reference light from the second light source.

11. The system of claim 10, wherein the system is arranged so that the difference in distance for reference light to travel to the detectors from the first and second light sources is selected so that beat frequencies generated by scattered light from the first light source and reference light from the first light source have no, or minimal, spectral overlap with beat frequencies generated by scattered light from the second light source and reference light from the second light source.

12. The system of claim 8, wherein the system is configured to control operation of the first and second light sources so that the two light sources do not emit light of the same wavelength at the same time and/or so that the first light source emits light that is incoherent with light from the second light source.

13. The system of claim 8, wherein the system is configured to control the light sources to operate sequentially so that the first light source emits light for a first time period while the second light source does not emit light, and then the second light source emits light for a second time period while the first light source does not emit light, and wherein at least one of the first and second time periods encompasses two or more wavelength sweeps.

14. The system of claim 8, wherein the system comprises a carrier channel combiner arranged to receive reference light from each of the first and second light sources; and wherein the carrier channel combiner is configured to combine the reference light from both the first light source and the second light source onto a carrier channel.

15. The system of claim 14, wherein the system comprises a carrier channel separator connected to the carrier channel and to reference channels connected to each of the detectors; and wherein the carrier channel separator is configured to separate light from the carrier channel into its constituent parts so that the reference light from the first light source is provided to each of the detectors via the reference channels and the reference light from the second light source is provided to each of the detectors via the reference channels.

16. The system of claim 1, wherein the first light source comprises an output light splitter configured to split the coherent light so that some of the light is delivered towards the subject's brain tissue and some of the light is delivered as reference light to each detector via the one or more reference channels.

17. The system of claim 1, wherein the first light source comprises a plurality of signal delivery channels arranged to receive the emitted light and to deliver said light towards the surface of the subject's head.

18. The system of claim 17, wherein the first light source comprises an optical switch configured to selectively apply light to each individual signal delivery channel in turn.

19. The system of claim 18, wherein the system is configured to control the optical switch to apply the light to a first of the signal delivery channels for a first time block, and to then apply the light to a second of the signal delivery channels for a second time block, and wherein the system is configured to control the optical switch so that at least one of the first time block and the second time block encompasses two or more wavelength sweeps.

20. The system of claim 1, wherein the system comprises a membrane arranged for attachment to the subject's head, and wherein each of the reference channels is coupled to the membrane, and wherein each of the reference channels is mechanically supported by the membrane.

21. The system of claim 1, wherein for each detector, the first input port, the second input port and the light combiner are provided on one integrated circuit.

22. A method for monitoring a subject's brain, the method comprising:

using a first light source to provide wavelength-swept emission of light and to deliver said wavelength-swept light towards the subject's brain tissue; and using a plurality of detectors to detect light scattered back from the subject's brain tissue at a plurality of different locations;

wherein the first light source is operated to deliver some of the wavelength-swept light it provides to each of the plurality of detectors as reference light via one or more reference channels;

wherein each of the detectors is operated to combine the reference light received from the first light source via the reference channel with the scattered light received from the subject's brain tissue to provide a combined light signal comprising a component at a beat frequency for the scattered and reference light; and wherein the method comprises providing an indication of effects in the subject's brain tissue based on changes in a distribution of a plurality of components at different beat frequencies of the combined light signal.

23. The method of claim 22, wherein the method further comprises using a second wavelength-swept light source to deliver wavelength-swept light both: (i) towards the subject's brain tissue, and (ii) to each of the detectors as reference light via one or more of the reference channels; and wherein each of the detectors is operated to combine the scattered light received from the subject's brain with at least one of: (i) the reference light received from the first light source via the one or more reference channels, and (ii) the reference light received from the second light source via the one or more reference channels, to provide the combined light signal.

24. The method of claim 22, wherein using the first light source to direct light towards the subject's brain tissue comprises sequentially providing the light to each of a plurality of different signal delivery channels which direct the light towards different regions of the subject's head.

25. A tangible non-transitory computer readable storage medium storing computer program instructions configured to, when executed, cause a controller to perform a method for monitoring a subject's brain, the method comprising:

using a first light source to provide wavelength-swept emission of light and to deliver said wavelength-swept light towards the subject's brain tissue; and using a plurality of detectors to detect light scattered back from the subject's brain tissue at a plurality of different locations;

wherein the first light source is operated to deliver some of the wavelength-swept light it provides to each of the plurality of detectors as reference light via one or more reference channels;

wherein each of the detectors is operated to combine the reference light received from the first light source via the reference channel with the scattered light received from the subject's brain tissue to provide a combined light signal comprising a component at a beat frequency for the scattered and reference light; and wherein the method comprises providing an indication of effects in the subject's brain tissue based on changes in a distribution of a plurality of components at different beat frequencies of the combined light signal.

* * * * *